US008206735B2

(12) United States Patent
Li et al.

(10) Patent No.: US 8,206,735 B2
(45) Date of Patent: Jun. 26, 2012

(54) PHARMACEUTICAL COMPOSITIONS FOR SUSTAINED RELEASE DELIVERY OF PEPTIDES

(75) Inventors: Yuhua Li, Newark, DE (US); Benjamin Chien, Newark, DE (US)

(73) Assignee: Foresee Pharmaceuticals, LLC, Newark, DE (US)

( * ) Notice: Subject to any disclaimer, the term of this patent is extended or adjusted under 35 U.S.C. 154(b) by 980 days.

(21) Appl. No.: 11/827,260

(22) Filed: Jul. 11, 2007

(65) Prior Publication Data

US 2008/0020016 A1  Jan. 24, 2008

Related U.S. Application Data

(60) Provisional application No. 60/830,011, filed on Jul. 11, 2006.

(51) Int. Cl.
A61K 47/48 (2006.01)

(52) U.S. Cl. .................. 424/426; 514/1.3; 514/10.4

(58) Field of Classification Search .................. None
See application file for complete search history.

(56) References Cited

U.S. PATENT DOCUMENTS

| | | | |
|---|---|---|---|
| 4,728,721 A | 3/1988 | Yamamoto et al. |
| 4,938,763 A | 7/1990 | Dunn et al. |
| 5,278,201 A | 1/1994 | Dunn et al. |
| 5,278,202 A | 1/1994 | Dunn et al. |
| 5,324,519 A | 6/1994 | Dunn et al. |
| 5,340,849 A | 8/1994 | Dunn et al. |
| 5,487,897 A | 1/1996 | Polson et al. |
| 5,599,552 A | 2/1997 | Dunn et al. |
| 5,681,873 A | 10/1997 | Norton et al. |
| 5,693,609 A | 12/1997 | Baker et al. |
| 5,702,716 A | 12/1997 | Dunn et al. |
| 5,733,950 A | 3/1998 | Dunn et al. |
| 5,736,152 A | 4/1998 | Dunn |
| 5,739,176 A | 4/1998 | Dunn et al. |
| 5,744,153 A | 4/1998 | Yewey et al. |
| 5,750,497 A | 5/1998 | Havelund |
| 5,759,563 A | 6/1998 | Yewey et al. |
| 5,780,044 A | 7/1998 | Yewey et al. |
| 5,792,469 A | 8/1998 | Tipton et al. |
| 5,945,115 A | 8/1999 | Dunn et al. |
| 5,990,194 A | 11/1999 | Dunn et al. |
| 6,143,314 A | 11/2000 | Chandrashekar et al. |
| 6,261,583 B1 | 7/2001 | Dunn et al. |
| RE37,590 E | 3/2002 | Leyden et al. |
| 6,355,657 B1 | 3/2002 | Osborne |
| 6,395,293 B2 | 5/2002 | Polson et al. |
| 6,461,631 B1 | 10/2002 | Dunn et al. |
| 6,528,080 B2 | 3/2003 | Dunn et al. |
| 6,565,874 B1 | 5/2003 | Dunn et al. |
| 2002/0012942 A1 | 1/2002 | McCarthy et al. |
| 2004/0228833 A1 | 11/2004 | Costantino et al. |

FOREIGN PATENT DOCUMENTS

| | | |
|---|---|---|
| EP | 0708179 A2 | 4/1996 |
| JP | 1254699 A | 10/1989 |
| WO | WO95/07931 | 3/1995 |
| WO | WO96/29342 | 9/1996 |
| WO | WO98/08871 | 3/1998 |
| WO | WO98/08872 | 3/1998 |
| WO | WO99/43708 | 9/1999 |
| WO | WO 02/065985 | 8/2002 |
| WO | WO 02/098446 | * 12/2002 |

OTHER PUBLICATIONS

Na, D.H., et al., Monitoring of peptide acylation inside degrading PLGA microspheres by capillary electrophoresis and MALDI-TOF mass spectrometry, *J Control Release* 92 (2003) 291-299.

Knudsen, L., et al., Potent Derivatives of Glucagon-like Peptide-1 with Pharmacokinetic Properties Suitable for Once Daily Administration, *J. Med. Chem.*, 2000, 43 1664-1669.

Kurtzhals, P., et al., Albumin binding of insulins acylated with fatty acids: characterization of the ligand-protein interaction and correlation between affinity and timing of the insulin effect in vivo, *Biochem J.* (1995) 312; 725-731.

Lindsay, D., et al., The Acetylation of Insulin, *Biochem J.* (1971) 121; 737-745.

Hashimoto, M. et al., Synthesis of Palmitoyl Derivatives of Insulin and Their Biological Activities, *Pharmacetical Research*, vol. 6, No. 2, 1989.

Havelund, S., The Mechanism of Protraction of Insulin Detemir, a Long-acting, Acylated Analog of Human Insulin, *Pharmaceutical Research*, vol. 21, No. 8, Aug. 2004.

Extended European Search Report dated May 12, 2010.

* cited by examiner

*Primary Examiner* — Christopher R. Tate
*Assistant Examiner* — Roy Teller
(74) *Attorney, Agent, or Firm* — VLP Law Group LLP

(57) ABSTRACT

The present invention provides methods of forming a solid, biodegradable implant in-situ in a body by administering a liquid pharmaceutical composition comprising an effective amount of a biocompatible, water-insoluble, biodegradable polymer and an effective amount of a therapeutic peptide covalently modified with one or more lipophilic or amphiphilic moieties, which are dissolved or dispersed in a biocompatible, water-soluble organic solvent. This invention also provides related compositions and methods.

18 Claims, 3 Drawing Sheets

PHARMACEUTICAL COMPOSITIONS FOR SUSTAINED RELEASE DELIVERY OF PEPTIDES

RELATED APPLICATIONS

This application claims priority of U.S. Provisional Application No. 60/830,011, filed Jul. 11, 2006, the contents of which are hereby incorporated into this application by reference.

Throughout this application, various publications are cited. The disclosure of these publications is hereby incorporated by reference into this application to describe more fully the state of the art to which this invention pertains.

BACKGROUND OF THE INVENTION

1. Field of the Invention

This invention relates to the field of controlled release delivery of therapeutic peptides and to compositions and methods useful for controlled release delivery of therapeutic peptides covalently modified with one or more lipophilic or amphiphilic molecules.

2. Description of the Related Art

Peptides, alternatively referred to as oligopeptides, polypeptides and proteins, have been widely used as therapeutic agents. The peptides may be conveniently produced by recombinant DNA technology or may be synthesized by well-established peptide synthesis technology. However, many peptides are susceptible to enzymatic degradation and have a very short in vivo circulation half-life. Therefore, most peptide medicines have been administered by injection, typically multiple times per day. It would be extremely beneficial if such peptides could be delivered in a controlled manner for extended periods of time to improve safety, efficacy and patient compliance.

Biodegradable polymers have been used for sustained delivery of therapeutic peptides. The peptide is generally incorporated into the polymeric composition and formed into desired shapes such as rods, wafers and microparticles outside of the body. These solid compositions can then be inserted into the body through an incision or injection. Alternatively and preferably, some of the polymeric compositions can be injected into the body as a liquid polymeric composition to form an implant in situ. Injectable liquid biodegradable polymeric compositions for in situ forming implants to deliver drugs in a controlled manner are described in the patent literature. The following references are believed to be representative in this area and are incorporated herein by reference: U.S. Pat. Nos. 6,565,874; 6,528,080; RE37,950; 6,461,631; 6,395,293; 6,355,657; 6,261,583; 6,143,314; 5,990,194; 5,945,115; 5,792,469; 5,780,044; 5,759,563; 5,744,153; 5,739,176; 5,736,152; 5,733,950; 5,702,716; 5,681,873; 5,599,552; 5,487,897; 5,340,849; 5,324,519; 5,278,202; 5,278,201; and 4,938,763. As described therein, a bioactive agent is dissolved or dispersed in a biodegradable polymer solution in a biocompatible organic solvent to provide a liquid composition. When the liquid composition is injected into the body, the solvent dissipates into the surrounding aqueous environment, and the polymer precipitates to form a solid or gel depot from which the bioactive agent is released over a long period of time as the polymer degrades. The use of such a delivery system was exemplified in the delivery of leuprolide acetate to treat advanced prostate cancer (Eligard™). Notwithstanding some success, those methods have not been entirely satisfactory for a large number of peptides that may be effectively delivered by such an approach.

For many therapeutic peptides, acylation and/or degradation of the peptides encapsulated in poly(DL-lactide-co-glycolide) microspheres have been observed during the release process [e.g., Na D H, Youn Y S, Lee S D, Son M O, Kim W A, DeLuca P P, Lee K C. J Control Release. 2003; 92(3):291-9]. The nucleophilic functional groups on peptides can not only react with the biodegradable polymer, but also can catalyze the degradation of the biodegradable polymer. It was also found that the acylation and/or degradation could occur much faster in polymer solution than in the solid state. For example, when octreotide acetate was mixed with 50/50 poly(DL-lactide-co-glycolide) having a carboxy terminal group solution in NMP, more than 80% of octreotide was acylated and/or degraded within 24 hours. The interaction/reaction between the peptide and polymer or its degradation products can occur during formulation, storage and administration. Therefore, in order to maintain the stability of the formulations, the peptide is typically supplied in a separate syringe while the rest of the components are packed in another syringe. The contents in the syringes are mixed just before use. However, because of the viscous nature of the polymer formulations, it is often difficult to mix the contents in two separated syringes by end users. The uniformity of the formulations prepared by the end user may vary significantly, contamination may also occur and, thus, the quality of the treatment can be compromised significantly. Furthermore, the in-situ formation of the solid implant from the injectable liquid polymer formulation is a slow process. Typically the solvent dissipation/diffusion process can take a few hours to several days or even longer depending on the solvent used. During this period, the presence of organic solvent could promote the interaction/reaction between peptide and polymer or its degradation products.

In addition, during the formation of the implant, the rate of diffusion of the peptide from the coagulating polymeric composition may be much more rapid than the rate of release that occurs from the subsequently formed solid implant. This initial "burst" release of peptide during implant formation may result in the loss or release of a large amount of the therapeutic peptides. If the peptide is particularly toxic or has a narrow therapeutic window, this initial release or burst is likely to lead to toxic side effects and may damage adjacent tissues. Therefore, the slow formation process of solid implant and the instability of the bioactive agents and/or excipients represent a very significant challenge to use this type of formulations for sustained release delivery of therapeutic peptides.

Covalent modification of peptides with lipophilic molecules, such as fatty acids, has been described to improve therapeutic efficacy by increasing circulating half-life in vivo through binding to albumin. [EP0708179-A2, EP0699686-A2, U.S. Pat. No. 6,268,343, Knudsen L B, Nielsen P F, Huusfeldt P O, Johansen N L, Madsen K, Pedersen F Z, Thogersen H, Wilken M, Agerso H. Potent derivatives of glucagon:like peptide-1 with pharmacokinetic properties suitable for once daily administration. J Med Chem. 2000, 43(9):1664-9; Kurtzhals P, Havelund S, Jonassen I, Kiehr B, Larsen U D, Ribel U, Markussen J. Albumin binding of insulins acylated with fatty acids: characterization of the ligand-protein interaction and correlation between binding affinity and timing of the insulin effect in vivo. Biochem J. 1995; 312 (3):725-31, and references cited therein]. Although the lipophilically modified peptides showed prolonged action in vivo compared with the native peptides, the plasma residence time of the modified peptides is limited by its binding affinity to albumin. One successful example is an acylated insulin (Detemir) which has a circulation half-life of 10.2±1.2 h. [Havelund S, Plum A, Ribel U, Jonassen I, Vølund A, Markussen J and Kurtzhals P, *Pharmaceutical Research*, 2004; 21 (8), 1498-1504]. This product has been approved for injection to treat patients with type I diabetes. However, it still needs to be administered to patients everyday. Therefore, there is a great need for a stable composition in which the rate of delivery of certain peptides can be more readily controlled, especially for a peptide that requires sustained release over a long period of time.

SUMMARY OF THE INVENTION

It was unexpectedly found that covalently modified peptides with one or more lipophilic and/or amphiphilic molecules could be formulated with biodegradable polymers resulting in significantly improved stability and sustained release profiles relative to non-conjugated peptides. Lipophilically and/or amphiphilically modified peptides could not only prevent the uncontrolled random acylation and degradation of the peptides during the formulation, storage and subsequent in vivo release processes, but could also reduce the undesired initial burst release of peptides. Such delivery systems allow higher concentrations of a therapeutic peptide to be safely incorporated into a biodegradable polymer delivery system. The efficacy of such products is also improved, since a much greater percentage of intact active peptide remains in the delivery system for sustained release and is not lost by degradation during the formulation, storage, administration and subsequent release in vivo.

Accordingly, the present invention provides novel pharmaceutical formulations for controlled, sustained release of therapeutic peptides. The compositions of the present invention comprise (a) a peptide that is covalently conjugated with one or more lipophilic molecule(s); (b) a biodegradable polymer; and (c) a pharmaceutically acceptable organic solvent. The peptides are covalently conjugated with one or more lipophilic molecule(s) in such a manner that the conjugated peptide retains most or all of the biological activities of the unconjugated peptide while it has an enhanced chemical resistance to reaction with the biodegradable polymer both in vitro and in vivo, relative to the unconjugated peptide. The lipophilically modified peptide is then formulated by dissolving or dispersing in a biodegradable polymer solution using a pharmaceutically acceptable organic solvent. The formulations of the present invention not only enhance the stability of the peptide during formulation, storage, administration and subsequent release, but also improve its release profiles with lower initial burst levels and sustained duration.

In another aspect, the present invention provides a composition comprising (a) a peptide that is covalently conjugated with one or more amphiphilic moieties; (b) a biodegradable polymer; and (c) a pharmaceutically acceptable organic solvent. The peptides are covalently conjugated with one or more amphiphilic moieties in such a manner that the conjugated peptide retains most or all of the biological activities of the unconjugated peptide while it has an enhanced chemical resistance to the reaction with the biodegradable polymer both in vitro and in vivo, relative to the unconjugated peptide. The amphiphilically modified peptide is then formulated by dissolving or dispersing in a biodegradable polymer solution using a pharmaceutically acceptable organic solvent. The formulations of the present invention not only enhance the stability of the peptide during formulation, storage, administration and subsequent release, but also improve its release profiles with lower initial burst levels and sustained duration.

The conjugated peptide also reduces the catalyzed degradation of the polymer by nucleophilic groups of the peptide.

Each of the compositions of the present invention may be a viscous or non-viscous liquid, gel or semi-solid that moves as a fluid so that it may be injected using a syringe. Each composition may be formed as an implantable polymeric matrix in vitro, or alternatively, it may be formed in-situ in the forms of a gel or a solid implant. The compositions can be administered by injection and/or implantation subcutaneously, intramuscularly, intraperitoneally, or intradermally. When administered to a subject, the controlled release of the peptide can be sustained for a desired period of time depending upon the composition of the implant. With the selections of the biodegradable polymer and other excipients, the duration of the sustained release of the peptide can be controlled over a period of time from several weeks to one year.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

Figure 1:
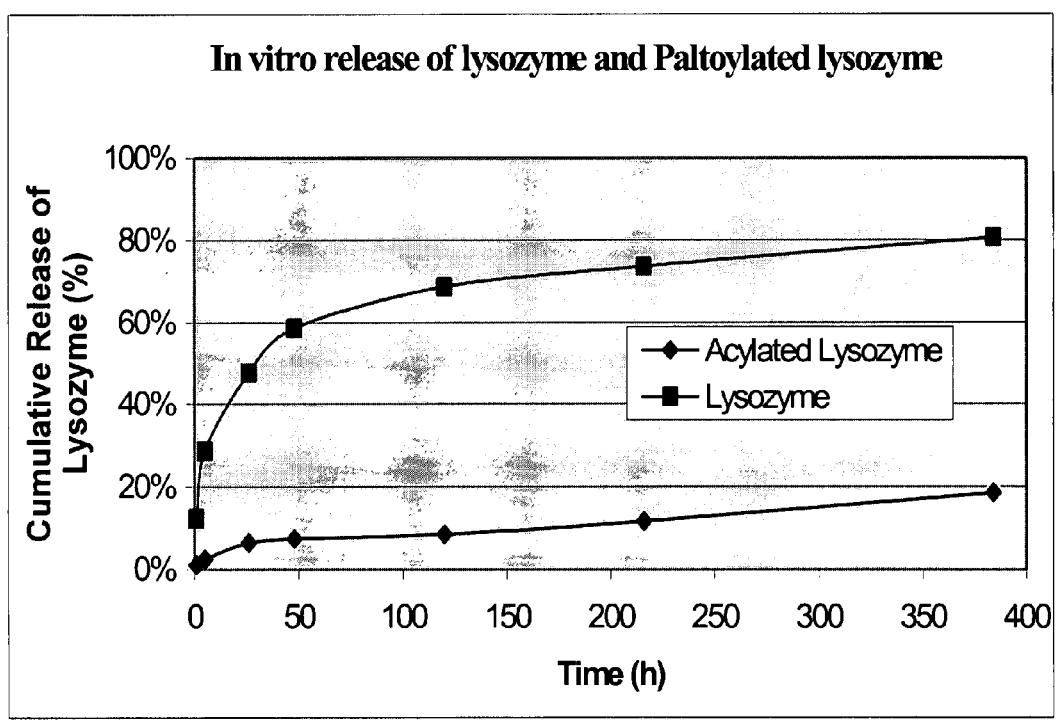
FIG. 1. In vitro release of lysozyme and palmitic acid acylated lysozyme from formulations in RG503H solution in mPEG350.

The present invention provides injectable liquid biodegradable polymeric compositions for forming a controlled release delivery system for peptides. The present invention also provides a method of manufacturing and a method of use thereof.

The compositions of the present invention comprise (a) a peptide that is conjugated, preferably covalently, with one or more lipophilic molecules; (b) a pharmaceutically acceptable, water insoluble, biodegradable polymer; and (c) a pharmaceutically acceptable organic solvent. The peptides are covalently conjugated with one or more lipophilic molecules in such a manner that the conjugated peptide retains most or all of the biological activities of the unconjugated peptide while it has an enhanced chemical resistance to the reaction with the biodegradable polymer both in vitro and in vivo, relative to the unconjugated peptide. The lipophilically modified peptide is then formulated by dissolving or dispersing in a biodegradable polymer solution using a pharmaceutically acceptable organic solvent. The formulations of the present invention not only enhance the stability of the peptide during formulation, storage, administration and subsequent release, but also improve its release profiles with lower initial burst levels and sustained duration.

In another aspect, the present invention provides a composition comprising (a) a peptide that is conjugated, preferably covalently, with one or more amphiphilic molecules; (b) a pharmaceutically acceptable, water insoluble, biodegradable polymer; and (c) a pharmaceutically acceptable organic solvent. The peptides are covalently conjugated with one or more amphiphilic molecules in such a manner that the conjugated peptide retains most or all of the biological activities of the unconjugated peptide while it has an enhanced chemical resistance to the reaction with the biodegradable polymer both in vitro and in vivo, relative to the unconjugated peptide. The amphiphilically modified peptide is then formulated by dissolving or dispersing in a biodegradable polymer solution using a pharmaceutically acceptable organic solvent. The formulations of the present invention not only enhance the stability of the peptide during formulation, storage, administration and subsequent release, but also improve its release profiles with lower initial burst levels and sustained duration. The conjugated peptide also reduces the catalyzed degradation of the polymer by nucleophilic groups of the peptide.

As used herein, the terms "a", "an" and "one" are meant to be interpreted as "one or more" and "at least one."

The term "peptide" is used synonymously with "polypeptide" and "protein." Non-limiting examples of therapeutic properties which a peptide can possess include anti-metabolic, anti-fungal, anti-inflammatory, anti-tumoral, anti-infectious, anti-biotic, nutrient, agonist, and antagonist properties.

More specifically, the peptides of the invention can be covalently modified with lipophilic or amphiphilic molecule(s). The peptides preferably contain one or more modifiable functional groups. Peptides useful in the preparation of the formulations of the invention include, but are not limited to, oxytocin, vasopressin, adrenocorticotropic hormone (ACTH), epidermal growth factor (EGF), platelet-derived growth factor (PDGF), prolactin, hormones such as luteinizing hormone, luteinizing hormone releasing hormone (LHRH), LHRH agonists, LHRH antagonists, growth hormones, growth hormone releasing factor, insulin, erythropoietin, somatostatin, glucagon, interleukin, interferon-alpha, interferon-beta, interferon-gamma, gastrin, tetragastrin, pentagastrin, urogastrone, secretin, calcitonin, enkephalins, endorphins, angiotensins, thyrotropin releasing hormone (TRH), tumor necrosis factor (TNF), parathyroid hormone (PTH), nerve growth factor (NGF), granulocyte-colony stimulating factor (G-CSF), granulocyte macrophage-colony stimulating factor (GM-CSF), macrophage-colony stimulating factor (M-CSF), heparinase, vascular endothelial growth factor (VEG-F), bone morphogenic protein (BMP), hANP, glucagon-like peptide (GLP-1), exenatide, peptide YY (PYY), ghrelin, renin, bradykinin, bacitracins, polymyxins, colistins, tyrocidine, gramicidins, cyclosporins, enzymes, cytokines, antibodies, vaccines, antibiotics, antibodies, glycoproteins, follicle stimulating hormone, kyotorphin, taftsin, thymopoietin, thymosin, thymostimulin, thymic humoral factor, serum thymic factor, colony stimulating factors, motilin, bombesin, dinorphin, neurotensin, cerulein, urokinase, kallikrein, substance P analogues and antagonists, angiotensin II, blood coagulation factors VII and IX, lysozyme, gramicidines, melanocyte stimulating hormone, thyroid hormone releasing hormone, thyroid stimulating hormone, pancreozymin, cholecystokinin, human placental lactogen, human chorionic gonadotrophin, protein synthesis stimulating peptide, gastric inhibitory peptide, vasoactive intestinal peptide, platelet derived growth factor, pigmentary hormones, somatomedin, chorionic gonadotropin, hypothalmic releasing factors, antidiuretic hormones, thyroid stimulating hormone, biphalin and prolactin.

As used herein, the term "lipophilic moiety" refers to any moiety having lipophilic characteristics and having a solubility in water at 20° C. less than 5 mg/ml, preferably less than 0.5 mg/ml. Such a lipophilic moiety is typically selected from $C_{3-39}$-alkyl, $C_{3-39}$-alkenyl, $C_{3-39}$-alkadienyl, tocopherol and steroidal residues. The terms "$C_{3-39}$-alkyl", "$C_{3-39}$-alkenyl" and "$C_{3-39}$-alkadienyl" are intended to cover straight chain and branched, preferably straight chain, saturated, monounsaturated and di-unsaturated hydrocarbon of 3-39 carbon atoms.

The covalent conjugation of a lipophilic moiety to a peptide leads to a lipophilically modified peptide that may have an improved therapeutic effect compared with the native peptide. This can typically be done by reacting a functional group such as an amine group in a peptide with an acid or other reactive groups in a lipophilic molecule. Alternatively, the conjugation between peptide and lipophilic molecule is accomplished through an additional moiety such as a bridge, spacer, or linkage moiety, which can be degradable or non-degradable. Some examples are disclosed in the prior art [e.g., fatty acid-acylated insulins are described in Japanese patent application 1,254,699. See also, Hashimoto, M., et al., Pharmaceutical Research, 6:171-176 (1989), and Lindsay, D. G., et al., Biochemical J., 121:737-745 (1971)]. More disclosures of fatty acid-acylated insulins and fatty acylated insulin analogs, and of methods for their synthesis, are found in U.S. Pat. No. 5,693,609, WO95/07931, U.S. Pat. No. 5,750,497, and WO96/29342. Further examples of acylated peptides are found in WO98/08871, WO98/08872, and WO99/43708. These disclosures describe lipophilically modified peptides and enable the preparation thereof.

As used herein, the term "amphiphilic moiety" refers to any moiety having both lipophilic and hydrophilic characteristics and soluble in both water and lipophilic solvents. The amphiphilic molecules used in the present invention are composed of lipophilic and hydrophilic moieties. The lipophilic moieties are preferably natural fatty acids or alkyl chains and those described above. The hydrophilic moieties are selected from polyethylene glycol, polyvinylpyrrolidone, sugar, and the like. The hydrophilic moieties are preferably polyethylene glycol (PEG) having less than 1000 ethylene glycol units. The size and composition of the lipophilic moieties and the hydrophilic moieties may be adjusted to obtain desired amphiphilicity.

As used herein, the terms "conjugated", "linked", "bonded", and the like, with reference to the peptide and other components of the modified peptide of the present invention, mean that the specified moieties are bonded to one another, preferably covalently, through a linker, bridge, spacer, or the like.

As used herein, the terms "linker", "bridge", "spacer", or the like refer to an atom or a group of atoms that link, preferably covalently, and for example, a lipophilic moiety to a therapeutic peptide.

In order to carry out covalent conjugation, a therapeutic peptide may have one or more suitable functional groups, or may be modified to include one or more suitable functional groups for covalent coupling to a lipophilic or amphiphilic moiety. Suitable functional groups include, for example, the following groups: hydroxyl group, amino group (primary amino or secondary amino group), thiol group, and carboxyl group. The lipophilic or amphiphilic moieties of the present invention may have one or more suitable functional groups, or may be modified to include one or more suitable functional groups for covalent coupling to a peptide. Suitable functional groups include, for example, the following groups: hydroxyl group, amino group (primary amino group or secondary amino group), thiol group, carboxyl group, aldehyde group, isocynato group, sulfonic acid group, sulfuric acid group, phosphoric acid group, phosphonic acid group, allylic halide group, benzylic halide group, substituted benzylic halide group, and oxiranyl group.

A therapeutic peptide may be directly or indirectly coupled with one or more lipophilic moieties through an ester group, amide group, secondary or tertiary amine group, carbamate group, sulfonate group, sulfate group, phosphate group, phosphonate group, or ether group.

In one embodiment of the present invention, palmitic acid was activated with N-hydroxysuccinimide and then reacted with amine groups on octreotide, an octapeptide, to form a conjugate through an amide linker between the palmityl lipophilic moiety and the peptide. There are two primary amine groups on octreotide. Both amine groups could be conjugated simultaneously or only one amine group could be selectively conjugated by adjusting the reaction conditions followed by separation.

In another embodiment, decanal, a lipophilic compound with an aldehyde end group, was reacted with the amine groups on octreotide to form a conjugate through a secondary amine linkage. Both amine groups could be conjugated simultaneously or only one amine group could be conjugated by adjusting the reaction conditions followed by separation.

In a further embodiment, palmitic acid was conjugated to lysozyme through its six amine groups at several ratios. When the ratio of palmitic acid to lysozyme is smaller than 6, the conjugation sites on lysozyme may be random depending upon the reactivity of each amine group.

In yet another embodiment, ghrelin is an acylated peptide through its hydroxyl group with an n-octanoyl moiety. Ghrelin is a gastric peptide that stimulates growth hormone secretion and increases adiposity. It is the first identified natural ligand for a previously cloned growth hormone secretagogue receptor which is present in the pituitary gland and the hypothalamic region of the brain.

A lipophilic moiety may be first covalently coupled to a hydrophilic moiety to form an amphiphilic molecule. The amphiphilic molecules of the present invention may have one or more suitable functional groups, or may be modified to have one or more suitable functional groups for covalent coupling to a peptide. Suitable functional groups are selected from hydroxyl group, amino group (primary amino group or secondary amino group), thiol group, carboxyl group, aldehyde group, isocynato group, sulfonic acid group, sulfuric acid group, phosphoric acid group, phosphonic acid group, allylic halide group, benzylic halide group, substituted benzylic halide group, and oxiranyl group.

A therapeutic peptide may be directly or indirectly coupled with one or more amphiphilic moieties through an ester group, amide group, secondary or tertiary amine group, carbamate group, sulfonate group, sulfate group, phosphate group, phosphonate group, or ether group.

Preferably, a therapeutic peptide is covalently conjugated to one or more amphiphilic molecules comprising (a) a hydrophilic moiety and (b) a lipophilic moiety, wherein the balanced hydrophilic and lipophilic characteristics of the amphiphilic molecule impart the conjugate with suitable solubility in biological fluid or aqueous solution.

More preferably, a therapeutic peptide is covalently conjugated to one or more amphiphilic molecules comprising (a) a linear polyethylene glycol moiety and (b) a lipophilic moiety, wherein the therapeutic peptide, the polyethylene glycol and the lipophilic moiety are conformationally arranged to have the lipophilic moiety exteriorly available for interaction with lipophilic environment or cell membranes. Such amphiphilically modified peptide has an enhanced chemical resistance to the reaction with the biodegradable polymer both in vitro and in vivo, relative to the unconjugated peptide.

Preferably, the amphiphilic molecule has the following general structure: L-S—$(OC_2H_4)_m$OH (Formula 1), wherein L is the lipophilic moiety preferably selected from $C_{3-39}$-alkyl, $C_{3-39}$-alkenyl, $C_{3-39}$-alkadienyl, tocopherol and steroidal residues, and wherein S is a linker selected from a group of an ester group, amide group, secondary or tertiary amine group, carbamate group, sulfonate group, sulfate group, phosphate group, phosphonate group, or ether group.

In one embodiment, an alkyl group of 16 carbons was covalently coupled to a polyethylene glycol molecule through an ether linkage. The resulting amphiphilic molecule has one hydroxyl group which can be activated or derivatized to react with suitable functional groups on peptides. In one embodiment of the present invention, the amphiphilic molecule was derivatized to have an aldehyde end group. Then the amphiphilic molecule was covalently conjugated to octreotide through the reaction with amine groups on octreotide followed by reduction reaction with $NaCNBH_3$. Both amine groups on octreotide could be conjugated simultaneously or only one amine group could be selectively conjugated by adjusting the reaction conditions followed by separation. The conjugate was formed through a secondary amine which does not change the charge characteristics of the unconjugated octreotide. This property may be useful to retain the activity of the peptide.

In another embodiment, the amphiphilic molecule monopalmityl poly(ethylene glycol) (Mn~1124) was activated with 4-nitrophenyl chloroformate. Then the amphiphilic molecule was covalently conjugated to octreotide through the reaction with amine groups on octreotide. Both amine groups on octreotide could be conjugated simultaneously or only one amine group could be selectively conjugated by adjusting the reaction conditions followed by separation.

Peptides covalently modified with one or more lipophilic or amphiphilic moieties include, for example, pharmaceutically acceptable salts and complexes of the modified peptide. The modification can be at one or more sites on the peptide. Such peptides also include, for example, site-specifically modified peptides and mixtures of mono-site and multiple-site modified peptides.

A "pharmaceutically acceptable salt" means a salt formed between any one or more of the charged groups in a peptide and any one or more pharmaceutically acceptable, non-toxic cations or anions. Organic and inorganic salts include, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, carbonic, and the like, or for example, ammonium, sodium, potassium, calcium, or magnesium.

The term "biodegradable water-insoluble polymer" includes any biocompatible (i.e., pharmaceutically acceptable) and biodegradable synthetic or natural polymer that can be used in vivo. This term also includes polymers that are insoluble or become insoluble in water or biological fluid at 37° C. The polymers may be purified, optionally, to remove monomers and oligomers using techniques known in the art (e.g., U.S. Pat. No. 4,728,721; U.S. patent application No. 2004/0228833). Some non-limiting examples of such polymers are polylactides, polyglycolides, polycaprolactones, polydioxanones, polycarbonates, polyhydroxybutyrates, polyalkylene oxalates, polyanhydrides, polyamides, polyesteramides, polyurethanes, polyacetals, polyorthocarbonates, polyphosphazenes, polyhydroxyvalerates, polyalkylene succinates and polyorthoesters, and copolymers, block copolymers, branched copolymers, terpolymers and combinations and mixtures thereof.

Suitable molecular weights for polymers may be determined by a person of ordinary skill in the art. Factors that may be considered when determining molecular weights include desired polymer degradation rate, mechanical strength, and rate of dissolution of polymer in solvent. Typically, a suitable range of molecular weights of polymers is of about 2,000 Daltons to about 150,000 Daltons with a polydispersity of from 1.1 to 2.8, depending upon which polymer is selected for use, among other factors.

According to the invention, pharmaceutical formulations of therapeutic peptides are prepared in the form of injectable solutions or suspensions of a polymer in a pharmaceutically acceptable solvent containing dispersed or solubilized lipophilically or amphiphilically modified peptides. By covalently coupling a peptide with a lipophilic or amphiphilic molecule, some reactive groups in peptide are protected and not available to interact with polymer in solution. Thus, the stability of the peptide and the polymer in the compositions of the present invention is improved by covalent modification of the peptide.

Therefore, the present invention provides a method of forming a solid, biodegradable implant in-situ, in a subject, comprising: (a) dissolving or dispersing a biocompatible, water-insoluble, biodegradable polymer and a therapeutic peptide covalently modified with one or more lipophilic or amphiphilic moieties in a biocompatible, water-soluble organic solvent to form a composition; the organic solvent being capable of dissipating or diffusing into a body fluid upon placement within a body tissue; and (b) administering the composition into an implant site within the body, so as to allow the organic solvent to dissipate or diffuse into the body fluids, and the polymer to coagulate or solidify to produce the biodegradable solid implant.

Additionally, the present invention provides for a liquid pharmaceutical composition for forming a biodegradable implant in-situ within a body, comprising an effective amount of a biocompatible, water-insoluble, biodegradable polymer and an effective amount of a therapeutic peptide covalently modified with one or more lipophilic or amphiphilic moieties, which are dissolved or dispersed in an effective amount of a biocompatible, water-soluble organic solvent; wherein the solvent is capable of dissipating or diffusing into a body fluid and the polymer is capable of coagulating or solidifying upon contact with body fluid.

Suitable peptides and lipophilic or amphiphilic molecules are those defined above. The molar ratio of peptide to lipophilic or amphiphilic molecule in the conjugate will vary, for example, from 1:1 to 1:10 according to the nature of the peptide.

Any suitable biodegradable polymer can be employed, provided the polymer is insoluble or becomes insoluble in aqueous medium or body fluid at 37° C. Suitable biodegradable polymers are those defined above.

The type, molecular weight, and amount of biodegradable polymer present in the compositions can influence the length of time in which the peptide is released from the controlled release implant. The selection of the type, molecular weight, and amount of biodegradable polymer present in the compositions to achieve desired properties of the controlled release implant can be performed by a person of ordinary skill in the art through routine experimentation.

Pharmaceutically acceptable organic solvents include, but are not limited to, N-methyl-2-pyrrolidone, N,N-dimethylformamide, dimethyl sulfoxide, propylene carbonate, caprolactam, triacetin, benzyl benzoate, benzyl alcohol, ethyl lactate, glyceryl triacetate, esters of citric acid, polyethylene glycols, alkoxypolyethylene glycols and polyethylene glycol acetates, or any combination thereof.

The criteria for the organic solvents of biodegradable polymers are that they are pharmaceutically acceptable and miscible to dispersible in aqueous medium or body fluid. The suitable organic solvent should be able to diffuse into body fluid so that the liquid composition coagulates or solidifies to form an implant in situ. Single and/or mixed solvents can be employed, and the suitability of such solvents can be determined readily by routine experimentation.

The pharmaceutical compositions of the invention typically contain peptides in a range of 0.1 to 40% w/v. In general, the optimal drug loading is dependent upon the period of release desired and the potency of the peptide. Obviously, for a peptide of low potency and a longer period of release, higher levels of incorporation may be required.

The viscosity of the injectable liquid compositions of the invention is determined by the molecular weight of the polymer and organic solvent used. For example, when poly(lactide-co-glycolide) is used, the solution of polyester in NMP has a lower viscosity than in mPEG350. Typically, when the same solvent is used, the higher the molecular weight and concentration of the polymer, the higher the viscosity. Preferably the concentration of the polymer in solution is below 70% by weight. More preferably, the concentration of the polymer in solution is between 20 to 60% by weight.

The release of lipophilically or amphiphilically modified peptides from these in-situ forming implants will follow the similar general rules for release of a drug from a monolithic polymeric device. The release of lipophilically or amphiphilically modified peptides can be affected by the size and shape of the implant, the loading of lipophilically or amphiphilically modified peptides within the implant, the permeability factors involving the lipophilically or amphiphilically modified peptides and the particular polymer, and the degradation of the polymer. Depending upon the amount of the modified peptides selected for delivery, the above parameters can be adjusted by one skilled in the art of drug delivery to give the desired rate and duration of release.

The amount of injectable composition administered will typically depend upon the desired properties of the controlled release implant. For example, the amount of injectable solution composition can influence the length of time in which the peptide is released from the controlled release implant.

According to the present invention, the compositions containing the lipophilically or amphiphilically modified peptides can be administered to a subject where sustained controlled release delivery of a peptide is desired. As used herein, the term "subject" is intended to include warm-blooded animals, preferably mammals, most preferably humans.

As used herein, the term "administered" is intended to refer to dispensing, delivering or applying a composition (e.g., pharmaceutical formulation) to a subject by any suitable route for delivery of the composition to the desired location in the subject, including delivery by injection and/or implantation subcutaneously, intramuscularly, intraperitoneally, or intradermally, and by administration to mucosal membranes to provide the desired dosage of a peptide based on the known parameters for treatment of the various medical conditions with the therapeutic peptides.

The term "controlled, sustained release delivery", as used herein, includes, for example, continual delivery of a therapeutic peptide in vivo over a period of time following administration, preferably at least several days to weeks or months. Controlled, sustained release delivery of the peptide can be demonstrated, for example, by the continued therapeutic effect of the agent over time (e.g., for octreotide, sustained delivery of the peptide can be demonstrated by continued GH reductions over time). Alternatively, sustained delivery of the agent may be demonstrated by detecting the presence of the agent in vivo over time.

In this application, the various embodiments set forth in the claims for the instant liquid pharmaceutical compositions are also envisioned, mutatis mutandis, for the instant methods for forming such compositions and the instant methods for forming solid implants.

EXAMPLES

The following examples illustrate the compositions and methods of the present invention. The following examples should not be considered as limitations, but should merely teach how to make the useful drug delivery systems.

Example 1

Preparation of Palmitoyl-Octreotide (PAL-OCT)

50 mg of octreotide acetate was dissolved in 1 mL of anhydrous DMSO containing 100 μL triethylamine (TEA). 40.2 mg of palmitic acid N-hydroxysuccinimide ester (Mw 353.50) was dissolved in 3 mL anhydrous DMSO and added to the peptide solution. The reaction was allowed to proceed for 3 hours at room temperature. The mixture was poured into diethylether to precipitate palmitoylated octreotide. The precipitate was washed with diethylether twice and then dried under vacuum. The resulting acylated peptide was in the form of a white powder.

Example 2

Preparation of Palmitoyl-Octreotide (PAL-OCT)

50 mg of octreotide acetate was dissolved in 1000 μL of anhydrous DMSO containing 100 μL TEA. 17.1 mg of palmitic acid N-hydroxysuccinimide ester (Mw 353.50) was dissolved in 3 mL anhydrous DMSO and added by direct injection to the peptide solution. The reaction was allowed to proceed overnight at room temperature. The mixture was poured into diethylether to precipitate palmitoylated octreotide. The precipitate was washed with diethylether twice and then dried under vacuum. The resulting acylated peptide was in the form of white powder.

Example 3

Preparation of Decanal-Octreotide (DSL-OCT)

50 mg of octreotide was dissolved in 2 mL of 20 mM sodium cyanoborohydride (Mw 62.84, NaCNBH$_3$) (2.51 mg) solution in 0.1 M acetate buffer at pH 5. 13.7 mg of Decanal (Mw 156.27) (OCT:DCL=1:2) was added by direct injection to the peptide solution. The reaction was allowed to proceed overnight at 4° C. The mixture was separated by centrifugation. The precipitated PAL-OCT was freeze-dried.

Example 4

Preparation of Palmitoyl-Lysozyme (PAL-Lyz, 3:1)

302 mg of Lysozyme (Mw 14,500) was dissolved in 1000 μL of anhydrous DMSO containing 200 μL TEA. 18.25 mg of Palmitic acid N-hydroxysuccinimide ester (Mw 353.50) was dissolved in 3 mL anhydrous DMSO and added by direct injection to the protein solution. The reaction was allowed to proceed for overnight at RT. The PAL-Lyz was precipitated in diethylether and the final product was freeze-dried after removing the organic solvent.

Example 5

Release of Palmitoyl-Lysozyme from Injectable Polymer Formulations

40% PLGA RG503H was prepared by appropriately dissolving the polymer in mPEG350. Then Palmitoyl-Lysozyme and lysozyme were mixed with the polymer solution at about 7% respectively. The formulations were thoroughly mixed to obtain uniform formulations.

In vitro release of lysozyme and palmitoylated lysozyme from injectable polymer solution: The formulation suspensions (about 100 mg) were injected into in 3 mL phosphate buffer saline solution at pH 7.4 with 0.1% sodium azide at 37° C. The receiving fluid was replaced at selected time points with fresh buffer solution, and the removed buffer solution was diluted appropriately with PB at pH 7.4 and analyzed for drug concentration by UV spectrophotometer at 280 nm against standard curves. FIG. 1 shows the cumulative release profiles of both acylated and native lysozyme. The native lysozyme showed significant release initially comparing to acylated lysozyme.

Example 6

Preparation of Palmitoyl-Lysozyme (PAL-Lyz, 5:1)

50 mg of lysozyme (Mw 14,500) was dissolved in water and pH was adjusted to 9.58. The solution was freeze-dried. Then the dried powder was dissolved in 3 mL DMSO. Then 322 μL of 20 mg/mL solution of palmitic acid N-hydroxysuccinimide ester (Mw 353.50) in anhydrous DMSO was added by direct injection to the protein solution. The reaction was allowed to proceed overnight at 4° C. The PAL-Lyz was precipitated in diethylether and the final product was freeze-dried after removing the organic solvent.

Example 7

Preparation of Palmitoyl-Lysozyme (PAL-Lyz, 13:1)

50 mg of lysozyme (Mw 14,500) was dissolved in water and pH was adjusted to 9.58. The solution was freeze-dried. Then the dried powder was dissolved in 3 mL DMSO. Then 799 μL of 20 mg/mL solution of palmitic acid N-hydroxysuccinimide ester (Mw 353.50) in anhydrous DMSO was added by direct injection to the protein solution. The reaction was allowed to proceed overnight at 4° C. The PAL-Lyz was precipitated in diethylether and the final product was freeze-dried after removing the organic solvent.

Example 8

Preparation of Palmitoyl-Lysozyme (PAL-Lyz)

Lysozyme is added to PAL-NHS in PBS (pH 8.0) containing 2% deoxycholate (DOC). The mixture is incubated at 37° C. for 6 hours. The mixture is centrifuged to remove the unreacted PAL-NHS. The product is dialyzed against PBS containing 0.15% DOC for 48 h. (PAL-NHS:Lyso=15:1).

Example 9

Release of Ghrelin from Injectable Polymer Formulations

40% PLGA RG503H was prepared by appropriately dissolving the polymer in mPEG350. Then ghrelin (Human, Rat 1-5) and deacylated ghrelin (Des-n-Octanoyl-[Ser]$^3$-ghrelin (Human, Rat 1-5)) were mixed with the polymer solution at about 6% respectively. The formulations were thoroughly mixed to obtain uniform formulations.

Figure 2:
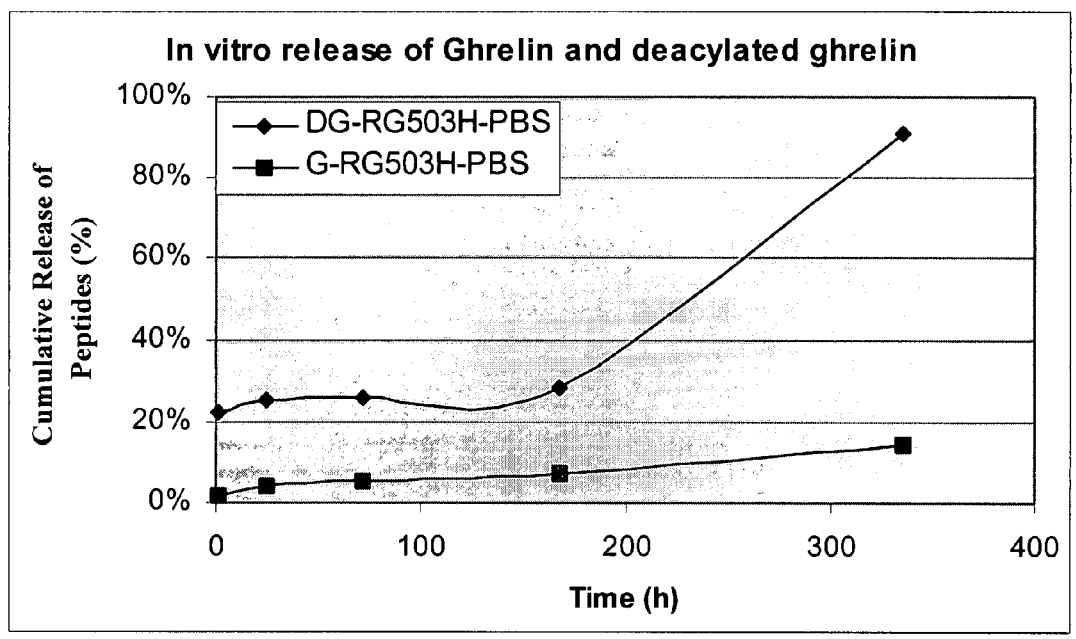
FIG. 2. In vitro release of ghrelin and deacylated ghrelin from formulations in RG503H solution in mPEG350.

The formulation suspensions (about 100 mg) were injected into in 3 mL phosphate buffer saline solution at pH 7.4 with 0.1% sodium azide at 37° C. The receiving fluid was replaced at selected time points with fresh buffer solution, and the removed buffer solution was diluted appropriately with PB at pH 7.4 and was analyzed for drug concentration by HPLC using corresponding standard curves. FIG. 2 shows the cumulative release of ghrelin and deacylated ghrelin in PBS. The deacylated ghrelin showed much faster release over the two week period tested. The ghrelin with a lipophilic moiety showed a much slower release rate.

Example 10

Preparation of Monopalmityl Poly(ethylene glycol)-Butyraldehyde, Diethyl Acetal A mixture of monopalmityl poly(ethylene glycol) (average Mn~124) (5.0 g, 4.45 mmoles) and toluene (75 mL) was azeotropically dried by distilling off toluene under reduced pressure. The dried monopalmityl poly(ethylene glycol), was dissolved in anhydrous toluene (50 mL) to which was added a 20% (w/w) solution of potassium tert-butoxide in THF (4.0 ml, 6.6 mmoles) and 4-chlorobutyraldehyde diethyl acetal (0.96 g, 5.3 mmoles, MW 180.67). The mixture was stirred at 100-105° C. overnight under an argon atmosphere. After cooling to room temperature, the mixture was filtered and added to 150 ml ethyl ether at 0-5° C. The precipitated product was filtered off and dried under reduced pressure.

Example 11

The Conjugation of Octreotide at N-terminal Amine Group with Monopalmityl Poly(ethylene glycol) (PAL-PEG-BA-OCT)

In a typical preparation, 201.6 mg of monopalmityl poly(ethylene glycol)-butyraldehyde, diethyl acetal (PAL-PEG-BADA) was dissolved in 10 mL of 0.1 M phosphoric acid (pH 2.1) and the resulting solution was heated at 50° C. for 1 h then cooled to room temperature. The pH of the solution was adjusted to 5.5 with 1 N NaOH and the resulting solution was added to a solution of 195.3 mg of octreotide in 3.5 mL of 0.1 M sodium phosphate buffer (pH 5.5). After 1 h, 18.9 mg of NaCNBH$_3$ was added to have a concentration of 20 mM. The reaction was continued overnight at room temperature. Then the reaction mixture was either dialyzed with a membrane having a MW cutoff of 2000 daltons or loaded on a preparative HPLC with a C-18 column. The purified conjugated octreotide was primarily a single compound with one primary amine (lysine), and one secondary amine (N-terminal).

Example 12

In vitro Release and Stability of Peptides and Biodegradable Polymer in Liquid Polymeric Compositions Poly(DL-lactide-co-glycolide) (PLGA) of an 85/15 ratio of lactide to glycolide having a polydispersity of 1.5 (DL-PLG85/15, IV: 0.28) was dissolved in N-methyl-2-pyrrolidone (NMP) to obtain a 50% solution by weight. The peptides were mixed with the PLGA solution in NMP to give a uniform injectable composition at ratios shown in Table 1.

TABLE 1

Injectable polymeric formulations tested

| Samples | Peptide (mg) | DLPLG 8515/NMP (mg) | Drug load (%, w/w) |
|---|---|---|---|
| Blank | 0 | 1000 | 0 |
| OCT | 60 | 940 | 6 |
| Pal-PEG-BA-OCT | 120 | 880 | 6 |

An aliquot from each formulation was taken for in vitro release in phosphate buffer at pH 7.4 containing 0.1% sodium azide at 37° C. and the remaining formulation was used to monitor the stability of the peptides and the polymer at room temperature over time. The time points are 0.125, 1, 2, 5, 7, 14, 21, and 28 days. Purity of the peptides in the sample was determined by HPLC. Molecular weight of the polymer was determined by gel permeation chromatography (GPC) using polystyrene standards with known molecular weights.

According to prior art, the presence of a nucleophilic group on a peptide can lead to an interaction between the peptide and the biodegradable polymer of a composition. The nucleophilic groups on the peptide can react with the biodegradable polymer to form acylated products and can catalyze the degradation of the biodegradable polymer. It is well known that when octreotide and poly(DL-lactide-co-glycolide) are combined, especially in an organic solution such as NMP, the octreotide will be acylated and the polymer will be degraded rapidly. The N-terminal conjugation of the octreotide in the present invention contains one primary amine, one secondary amine and one C-terminal carboxylic acid group and is expected to interact and/or react with the polymer similarly to the octreotide itself. However, it has been unexpectedly found that the covalently conjugated octreotide of the present invention prevented the acylation reaction and significantly reduced the degradation rate of the polymer relative to the unmodified octreotide. As described in the prior art and shown in Table 2, when the octreotide was mixed with poly(DL-lactide-co-glycolide) solution in NMP, the octreotide was acylated more than 80% within 24 hours at room temperature and almost completely reacted after 7 days. However, the covalently conjugated octreotide was stable even after 56 days under the same condition. As shown in Table 3, the molecular weight of the polymer in the formulation containing octreotide decreased rapidly at room temperature. After 21 days, the molecular weight of the polymer was reduced by 50%. However, for the polymer in the formulation containing covalently conjugated octreotide, more than 90% of the original molecular weight was retained.

TABLE 2

Stability of the peptides in liquid polymeric formulations

| Time (Day) | Octreotide | PAL-PEG-BA-OCT |
|---|---|---|
| 7 | 2.3 | 99.6 |
| 14 | 0.6 | 100.0 |
| 21 | 0.3 | 100.0 |
| 56 | 0.0 | 100.0 |

TABLE 3

Stability of the polymer in liquid polymeric formulations

| Time (day) | 8515PLG in NMP | Octreotide | PAL-PEG-BA-OCT |
|---|---|---|---|
| 0 | 100 | 100 | 100 |
| 0.1 | 100.0 | 95.8 | 100.6 |
| 1 | 99.2 | 75.3 | 99.8 |
| 2 | 99.0 | 66.1 | 98.8 |
| 3 | 102.0 | 65.3 | 100.4 |
| 7 | 98.9 | 59.0 | 98.6 |
| 14 | 100.8 | 57.1 | 98.1 |
| 21 | 98.2 | 51.3 | 92.2 |

As disclosed in the prior art, in order to maintain the stability of bioactive agents and excipients in a formulation, generally, the bioactive agent is packed separately from other components of the formulation, such as in the commercial leuprolide formulation Eligard. Then all the ingredients are mixed immediately before use. Although, such preparation may prevent the interaction between peptides and biodegradable polymers during storage, it does not prevent any interaction after they are mixed. The interaction between the peptides and the polymer can occur during administration and subsequent release in vitro or in vivo.

Figure 3:
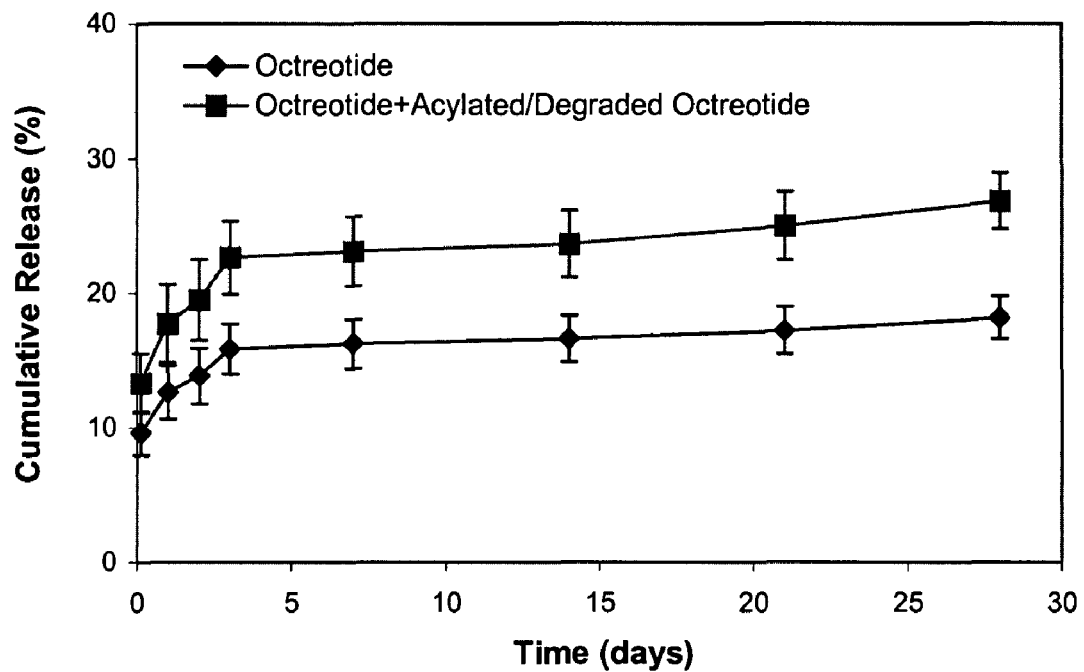
FIG. 3. In vitro release of octreotide from formulation in DLPLG85/15 (IV 0.28) solution in NMP FIG. 4. In vitro release of modified octreotide (Pal-PEG-BA-OCT) from formulation in DLPLG85/15 (IV 0.28) solution in NMP.

When an aliquot from each formulation after preparation was taken to conduct in vitro release in phosphate buffer at pH 7.4 containing 0.1% sodium azide at 37° C., it was surprisingly found that the interaction between octreotide and the polymer occurred during the mixing and the subsequent release in vitro. As shown in FIG. 3, about 30% of the octreotide detected in the releasing medium was degraded or reacted with the polymer within 3 hours. And more than 50% of the octreotide detected in the releasing medium was degraded or acylated after 28 days. After 28 days, the polymer matrix was dissolved in acetonitrile, and the polymer was precipitated using water. The octreotide was analyzed by HPLC. It was found that more than 50% of the octreotide remaining in the polymer matrix was also acylated. Such degradation and/or acylation of the octreotide would significantly reduce the availability of the native octreotide and may produce undesired toxic by-products. It would be highly advantageous to prevent such interaction between the peptide and the polymer.

Figure 4:
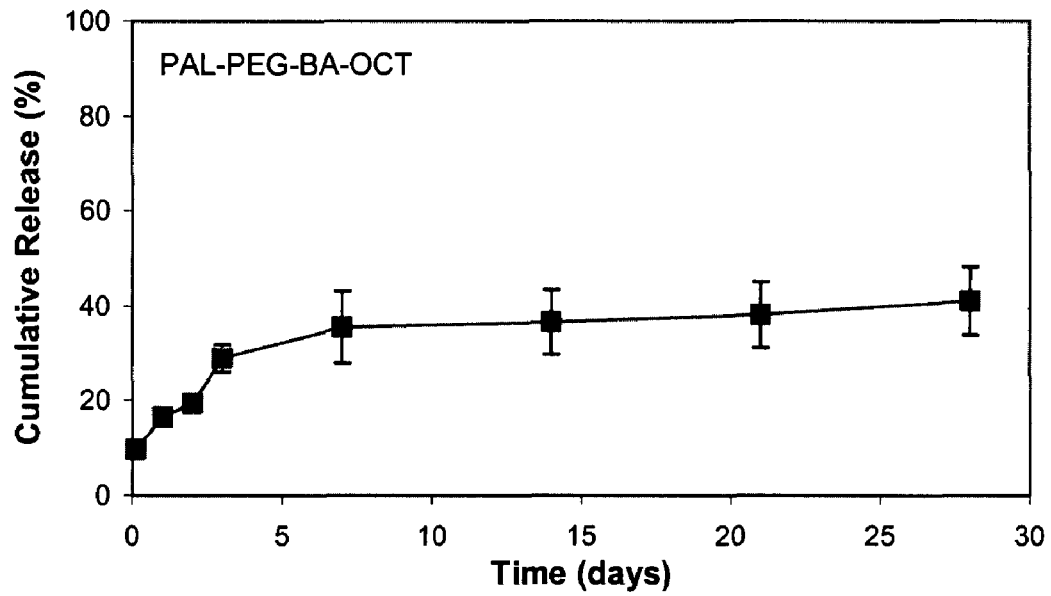

FIG. 4 shows the in vitro release of the covalently conjugated octreotide Pal-PEG-BA-OCT. Although the modified octreotide contains similar neucleophiles as the unmodified octreotide, it was surprisingly found that no degradation of the modified octreotide was detected in the releasing medium and in the polymer matrix over 28 days. The results indicate that the covalent conjugation of the peptide with an amphiphilic moiety such as monopalmityl poly(ethylene glycol) can prevent or significantly reduce the interaction and/or reaction between peptides and biodegradable polymers.

Example 13

Preparation of Monopalmityl Poly(ethylene glycol) Activated with 4-nitrophenyl chloroformate (NPC)

A mixture of monopalmityl poly(ethylene glycol) (average Mn~1124) (10.0 g, 8.9 mmoles) and benzene (100 mL) was azeotropically dried by distilling off 50 mL benzene under reduced pressure. The reaction mixture was cooled to 30° C., followed by the addition of anhydrous pyridine (0.809 mL, 10 mmol) under Argon and 4-nitrophenyl chloroformate (2.015 g, 10.0 mmoles). Once addition was complete, the reaction was stirred at 45° C. for 2 h followed by stirring overnight at room temperature.

The reaction mixture was then filtered, followed by removal of the solvent from the filtrate by distillation in vacuo. The residue was re-crystallized from 2-propanol to yield 8.2 g of the product (PAL-PEG-NPC).

Example 14

The Conjugation of Octreotide with Monopalmityl Poly(ethylene glycol) (PAL-PEG-OCT)

236.5 mg of PAL-PEG-NPC was added to a solution of 239 mg of octreotide in 10 mL of 50 mM sodium borate buffer (pH 9). The solution was magnetically stirred continuously overnight. The final solution was dialyzed using a membrane of MW cutoff of 2000. The dialyzed solution was freeze-dried and analyzed by HPLC. The results indicate the modified peptide is a mixture of monosite and multiple site conjugated octreotide.

The invention is not limited by the embodiments described above which are presented merely as examples and can be modified in various ways within the scope of protection defined by the appended patent claims.

We claim:

1. A liquid polymeric pharmaceutical composition for controlled release of a therapeutic polypeptide, comprising effective amounts of: (a) a pharmaceutically acceptable, water insoluble, biodegradable polymer selected from the group consisting of a polylactide, a polyglycolide, a polycaprolactone, a polydioxanone, a polycarbonate, a polyhydroxybutyrate, a polyalkylene oxalate, a polyanhydride, a polyamide, a polyesteramide, a polyurethane, a polyacetal, a polyorthocarbonate, a polyphosphazene, a polyhydroxyvalerate, a polyalkylene succinate, and a polyorthoester, and copolymers, block copolymers, branched copolymers, terpolymers and combinations and mixtures thereof; (b) a pharmaceutically acceptable organic solvent which solubilizes the biodegradable polymer; and (c) a therapeutic polypeptide conjugated with one or more lipophilic moieties, wherein the composition is in the form of an injectable viscous liquid and is capable of forming a controlled release implant by dissipation or dispersion of the organic solvent within a subject's body; and wherein the composition has a higher in vitro stability and a lower initial burst release than the composition would were the therapeutic polypeptide not conjugated to the lipophilic moieties.

2. A method for forming the liquid polymeric pharmaceutical composition of claim 1, comprising the steps of (a) dissolving a pharmaceutically acceptable, water-insoluble, biodegradable polymer—selected from the group consisting of a polylactide, a polyglycolide, a polycaprolactone, a polydioxanone, a polycarbonate, a polyhydroxybutyrate, a polyalkylene oxalate, a polyanhydride, a polyamide, a polyesteramide, a polyurethane, a polyacetal, a polyorthocarbonate, a polyphosphazene, a polyhydroxyvalerate, a polyalkylene succinate, and a polyorthoester, and copolymers, block copolymers, branched copolymers, terpolymers and combinations and mixtures thereof, in a pharmaceutically acceptable organic solvent to form a polymer solution; and (b) admixing the polymer solution with an effective amount of a therapeutic polypeptide conjugated with one or more lipophilic moieties to form said liquid polymeric pharmaceutical composition.

3. A method for forming a solid, biodegradable implant in-situ for sustained delivery of a therapeutic polypeptide comprising administering the liquid polymeric pharmaceutical composition of claim 1 into an implant site within a subject's body.

4. A method for forming a solid, biodegradable implant in-situ for sustained delivery of a therapeutic polypeptide comprising (a) forming a liquid polymeric pharmaceutical composition according to the method of claim 2, and (b) administering the resulting composition into an implant site within a subject's body.

5. The composition of claim 1, wherein the polypeptide and the lipophilic moiety or moieties are covalently conjugated.

6. The composition of claim 1, wherein the polypeptide and the lipophilic moiety or moieties are covalently conjugated through a spacer, a bridge or a linker group.

7. The composition of claim 1, wherein the polypeptide is selected from the group consisting of oxytocin, vasopressin, adrenocorticotropic hormone (ACTH), epidermal growth factor (EGF), platelet-derived growth factor (PDGF), prolactin, luteinizing hormone, luteinizing hormone releasing hormone (LHRH), an LHRH agonist, an LHRH antagonist, a growth hormone, growth hormone releasing factor, insulin, erythropoietin, somatostatin, glucagon, interleukin, interferon-alpha, interferon-beta, interferon-gamma, gastrin, tetragastrin, pentagastrin, urogastrone, secretin, calcitonin, an enkephalin, an endorphin, an angiotensin, thyrotropin releasing hormone (TRH), tumor necrosis factor (TNF), parathyroid hormone (PTH), nerve growth factor (NGF), granulocyte-colony stimulating factor (G-CSF), granulocyte macrophage-colony stimulating factor (GM-CSF), macrophage-colony stimulating factor (M-CSF), heparinase, vascular endothelial growth factor (VEG-F), bone morphogenic protein (BMP), hANP, glucagon-like peptide (GLP-1), exenatide, peptide YY (PYY), Ghrelin, renin, bradykinin, a bacitracin, a polymyxin, a colistin, tyrocidine, a gramicidin, a cyclosporin, an enzyme, a cytokine, an antibody, a vaccine, an antibiotic, a glycoprotein, follicle stimulating hormone, kyotorphin, taftsin, thymopoietin, thymosin, thymostimulin, thymic humoral factor, serum thymic factor, a colony stimulating factor, motilin, bombesin, dinorphin, neurotensin, cerulein, urokinase, kallikrein, a substance P analogue, a substance P antagonist, angiotensin II, blood coagulation factors VII and IX, lysozyme, a gramicidine, melanocyte stimulating hormone, thyroid hormone releasing hormone, thyroid stimulating hormone, pancreozymin, cholecystokinin, human placental lactogen, human chorionic gonadotrophin, protein synthesis stimulating peptide, gastric inhibitory peptide, vasoactive intestinal peptide, and platelet derived growth factor.

8. The composition of claim 1, wherein the polypeptide is selected from the group consisting of ACTH, glucagon, somatotropin, thymosin, a pigmentary hormone, somatomedin, chorionic gonadotropin, a hypothalmic releasing factor, an antidiuretic hormone, thyroid stimulating hormone, biphalin and prolactin.

9. The composition of claim 1, wherein the polypeptide is selected from the group consisting of epidermal growth factor (EGF), an LHRH agonist, an LHRH antagonist, a growth hormone, growth hormone releasing factor, octreotide, interferon-alpha, interferon-beta, interferon-gamma, calcitonin, parathyroid hormone (PTH), glucagon-like peptide (GLP-1), and peptide YY (PYY).

10. The composition of claim 1, wherein the polypeptide is glucagon like peptide 1 (GLP-1).

11. The composition of claim 1, wherein the polypeptide is exendin.

12. The composition of claim 1, wherein the polypeptide is octreotide.

13. The composition of claim 1, wherein the polypeptide is insulin.

14. The composition of claim 1, wherein the lipophilic moiety is selected from the group consisting of C3-39-alkyl, C3-39-alkenyl, C3-39-alkadienyl, tocopherol and steroidal compounds.

15. The composition of claim 14, wherein each of the C3-39-alkyl, C3-39-alkenyl and C3-39-alkadienyl is (i) straight chain or branched, and (ii) saturated, monounsaturated or di-unsaturated.

16. The composition of claim 1, wherein the lipophilic moiety is a lipid.

17. The composition of claim 1, wherein the biodegradable polymer is selected from the group consisting of a polylactic acid and a polyglycolic acid, and copolymers thereof.

18. The composition of claim 1, wherein the organic solvent is selected from the group consisting of N-methyl-2-pyrrolidone, N,N-dimethylformamide, dimethyl sulfoxide, propylene carbonate, caprolactam, triacetin, benzyl benzoate, benzyl alcohol, ethyl lactate, glyceryl triacetate, an ester of citric acid, polyethylene glycol, alkoxypolyethylene glycol, polyethylene glycol acetate, or any combination thereof.

* * * * *